United States Patent
Guala

(10) Patent No.: US 10,888,652 B2
(45) Date of Patent: Jan. 12, 2021

(54) FOOT VALVE FOR DRIP CHAMBERS OF MEDICAL INFUSION OR TRANSFUSION APPARATUSES

(71) Applicant: INDUSTRIE BORLA S.p.A., Moncalieri (IT)

(72) Inventor: Gianni Guala, Turin (IT)

(73) Assignee: INDUSTRIE BORLA S.P.A, Turin (IT)

( * ) Notice: Subject to any disclaimer, the term of this patent is extended or adjusted under 35 U.S.C. 154(b) by 248 days.

(21) Appl. No.: 16/073,953

(22) PCT Filed: Feb. 1, 2017

(86) PCT No.: PCT/IB2017/050525
§ 371 (c)(1),
(2) Date: Jul. 30, 2018

(87) PCT Pub. No.: WO2017/134564
PCT Pub. Date: Aug. 10, 2017

(65) Prior Publication Data
US 2019/0060560 A1 Feb. 28, 2019

(30) Foreign Application Priority Data
Feb. 5, 2016 (IT) ........................ 102016000012348

(51) Int. Cl.
*A61M 5/14* (2006.01)
*A61M 39/24* (2006.01)
*A61M 5/168* (2006.01)

(52) U.S. Cl.
CPC ...... *A61M 5/1411* (2013.01); *A61M 5/16881* (2013.01); *A61M 2039/242* (2013.01);
(Continued)

(58) Field of Classification Search
CPC .. A61M 5/1411; A61M 5/162; A61M 5/1689; A61M 5/40; A61M 5/16881;
(Continued)

(56) References Cited

U.S. PATENT DOCUMENTS

| 4,078,563 A | 3/1978 | Tuseth |
| 4,640,306 A | 2/1987 | Fan |

(Continued)

FOREIGN PATENT DOCUMENTS

| CN | 102772842 A | 11/2012 |
| CN | 102772842 A * | 4/2014 |

(Continued)

OTHER PUBLICATIONS

Specification English Translation of CN102772842 (Year: 2012).*
(Continued)

*Primary Examiner* — Jenna Zhang
(74) *Attorney, Agent, or Firm* — Heslin Rothenberg Farley & Mesiti P.C.; Victor A. Cardona, Esq.

(57) ABSTRACT

A foot valve for drip chambers of medical infusion or transfusion apparatuses having an annular valve seat with which a float obturator axially displaceable between a position for closing and a position for opening the valve seat cooperates. A containment cage bush has an elastically deformable lateral wall within which the float obturator floats in a guided fashion, and the lateral wall of the containment bush and the float have respective mutually facing surfaces configured such that a radial deformation of the containment bush applies an axial thrust to the float obturator in the direction of moving it apart from the annular valve seat.

4 Claims, 6 Drawing Sheets

(52) U.S. Cl.
CPC ............. *A61M 2039/2433* (2013.01); *A61M 2039/2473* (2013.01)

(58) Field of Classification Search
CPC .... A61M 2039/242; A61M 2039/2433; A61M 2039/2473; A61M 39/24; Y10T 137/7319; Y10T 137/7426; Y10T 137/7436; F16K 31/20; F16K 31/22; F16K 33/00
See application file for complete search history.

(56) References Cited

U.S. PATENT DOCUMENTS

| | | | | |
|---|---|---|---|---|
| 5,405,333 | A * | 4/1995 | Richmond | A61J 1/10 604/257 |
| 5,730,730 | A | 3/1998 | Darling, Jr. | |
| 6,695,004 | B1 * | 2/2004 | Raybuck | A61M 5/1411 137/15.26 |
| 2002/0065491 | A1 | 5/2002 | Guala | |
| 2011/0125103 | A1 * | 5/2011 | Rondeau | A61M 5/16813 604/251 |

FOREIGN PATENT DOCUMENTS

| | | |
|---|---|---|
| DE | 202015103791 U1 | 1/2016 |
| EP | 1693077 A2 | 8/2006 |

OTHER PUBLICATIONS

Drawing of CN102772842 (Year: 2012).*
Plastic hardness qualifies the resistance to penetration of a plastic by a harder body. The harder material wears or scratches the softer material obtained from Omnexus at https://omnexus.specialchem.com/polymer-properties/properties/hardness-introduction (Year: 2017).*
The Definitive Guide to Polypropylene (PP) obtained from Omnexus at https://omnexus.specialchem.com/selection-guide/polypropylene-pp-plastic#Properties (Year: 2017).*
International Search Report and Written Opinion of the International Searching Authority for PCT/IB2017/050525 dated Mar. 20, 2017.
First Office Action from China National Intellectual Property Administration dated Mar. 31, 2020.

* cited by examiner

FOOT VALVE FOR DRIP CHAMBERS OF MEDICAL INFUSION OR TRANSFUSION APPARATUSES

CROSS REFERENCE TO RELATED APPLICATIONS

This application is a national stage filing under section 371 of International Application No. PCT/IB2017/050525, filed on Feb. 1, 2017, published in English on Aug. 10, 2017 as WO2017/134564A1 and which claims priority to Italian Application No. 102016000012348, filed on Feb. 5, 2016, the entire disclosure of these applications being hereby incorporated herein by reference.

FIELD OF THE INVENTION

The present invention generally regards medical infusion or transfusion apparatuses and more in particular it regards a drip chamber for the metered supply of a medical liquid, typically contained in a bag or a bottle, to a patient.

STATE OF THE ART

Drip chambers thus made consist of a hollow elongated cylindrical body having a bottom wall with an outlet opening. The passage through the outlet opening is controlled by a foot valve including an annular valve seat with which a float obturator axially displaceable in use between an open position, in presence of the liquid inside the drip chamber, and a closed position should the liquid become exhausted, cooperates. Then, the re-opening of the valve may be carried out manually, due to a radial thrust applied from outside the float obturator through the lateral wall of the drip chamber, which is radially elastically deformable, so as to move the float obturator apart from the valve seat.

The float obturator is conventionally constituted by a simple ball element free to move inside the drip chamber body. Though simple and economic, this configuration can reveal functional problems in that—in use—should the drip chamber not be perfectly vertical, the closure of the ball obturator on the annular valve seat may be inaccurate and incomplete, with the risk of failing to completely close the flow of air through the outlet opening in the bottom wall of the drip chamber.

Document US-2011/0125103A1 discloses a drip chamber provided with a foot valve including an obturator fixed to the drip chamber body and a valve seat axially displaceable with respect to the obturator by rotating a sleeve fastened to an elastically deformable tubular appendage of the drip chamber.

SUMMARY OF THE INVENTION

The object of the present invention is to overcome such drawback. This object is attained thanks to a foot valve of the type defined in the pre-characterising part of claim 1, whose peculiar feature resides in that it comprises a containment cage bush having an elastically deformable lateral wall within which the float obturator floats in a guided fashion. The lateral wall of the containment bush and the float have respective surfaces mutually faced and configured such that a radial deformation of the containment bush applies an axial thrust to the float obturator in the direction of moving it apart from the annular valve seat.

Thanks to this solution, the movement of the float obturator from the opening position, in presence of liquid in the drip chamber, to the closing position, in absence of liquid, occurs in a guided and thus controlled manner in use, thus avoiding the risk of an inaccurate or imperfect closure. The re-opening of the foot valve can also be carried out in a more efficient and safe manner thanks to the fact that, contrary to conventional solutions, the travel of the obturator floating in the drip chamber is not free but limited by the containment cage bush.

According to the invention, the containment bush has a flat base forming the annular valve seat, and the float is provided with a soft disk-like membrane which rests against such base in the valve closure position.

The containment bush is advantageously formed by a crown of elastically deformable axial sectors whose free ends have diverging portions facing a corresponding diverging annular wall of the float.

BRIEF DESCRIPTION OF THE DRAWINGS

The invention will now be described in detail, purely by way of non-limiting example, with reference to the attached drawings, wherein.

DETAILED DESCRIPTION OF THE INVENTION

Figure 1:
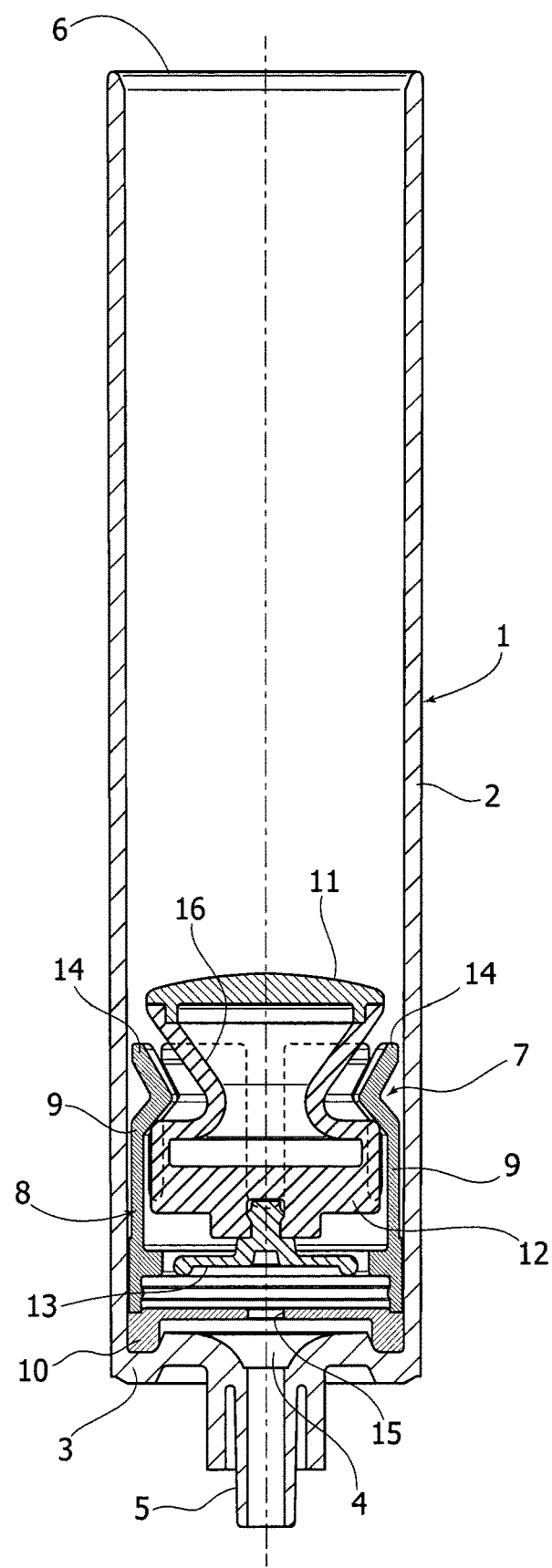
FIG. 1 is an axial sectional schematic view of a drip chamber of a medical infusion or transfusion apparatus provided with a foot valve according to the invention, represented in opening position.

Initially referring to FIG. 1, a drip chamber for medical infusion or transfusion apparatuses, formed by a hollow elongated cylindrical body made of plastic material having a radially elastically deformable lateral wall 2 and a bottom wall 3 provided with an outlet opening 4 communicating with a tubular connector 5 for connecting the drip chamber to a flexible pipe, is indicated with 1.

The end of the drip chamber 1 opposite to the bottom wall 3, indicated with 6, is designed to sealingly receive a piercing element of the known type, not represented.

Arranged inside the drip chamber 1 is a foot valve, generally indicated with 7, having the function of controlling the flow through the outlet opening 4: such passage should be open in presence of liquid inside the drip chamber 1, and it should automatically close should the liquid finish.

According to the invention, the foot valve 7 comprises a containment cage bush 8, formed by a crown of elastically deformable axial sectors 9 projecting from a flat base 10 sealingly fixed between the lateral wall 2 and the bottom wall 3 of the drip chamber 1 and forming an annular valve seat 15.

A float obturator 11, formed by a hollow body, made of two pieces as illustrated or a single piece, having a lower wall 12 and a shaped lateral wall 16, floats inside the cage bush 8 in a guided fashion.

A disk-like membrane 13 made of soft material, axially facing the annular valve seat 15 of the containment cage bush 8 is fixed outside the lower wall 12.

The lateral wall 16 of the float obturator 11 has an annular surface diverging towards the end 6 of the drip chamber 1, which is arranged facing correspondingly divergent portions 14 of the deformable axial sectors 9 of the containment cage bush 8.

Figure 2:
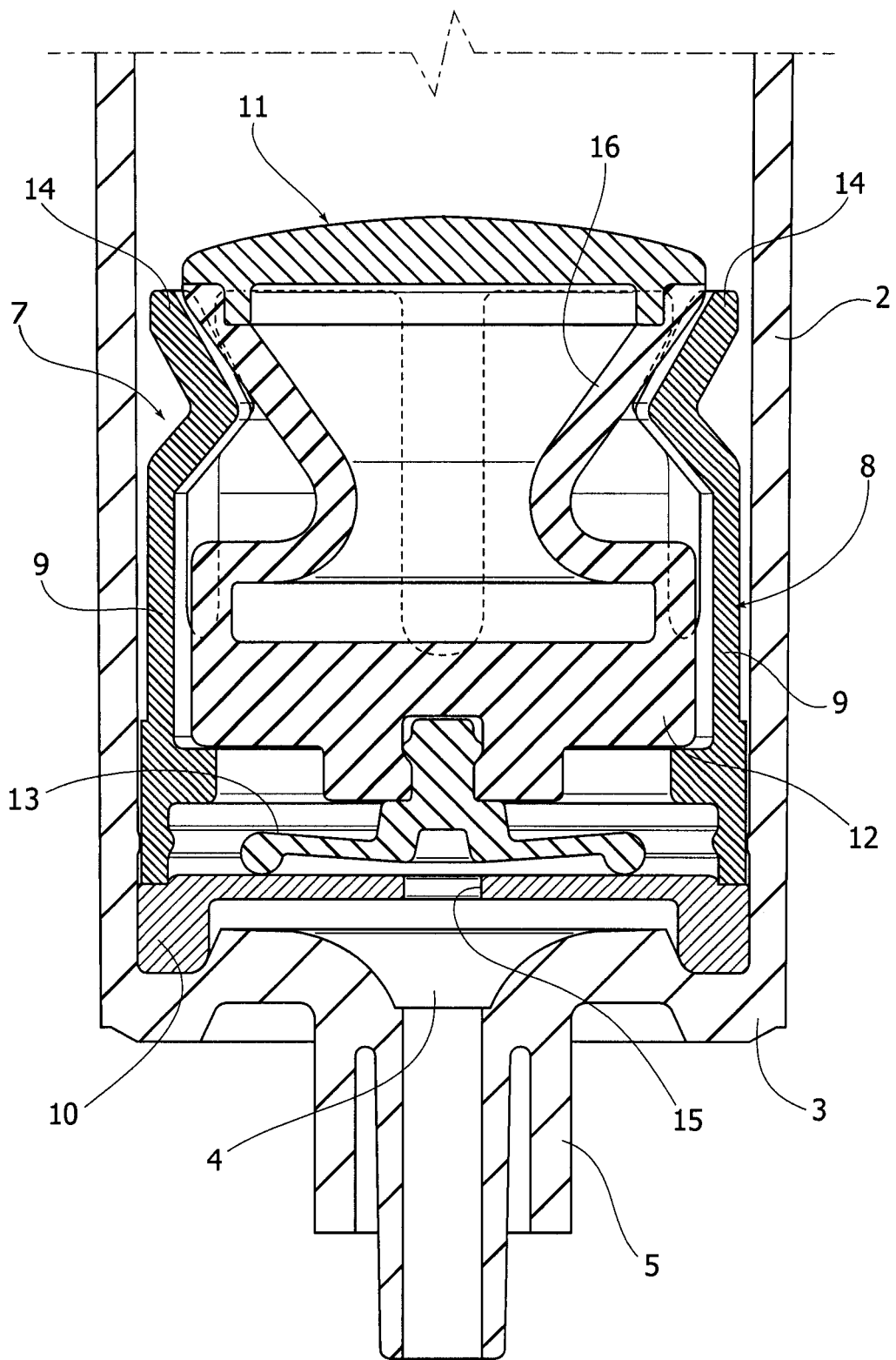
FIG. 2 shows—in larger detail—a part of FIG. 1 with the foot valve in closing position.

In the position for closing the foot valve 7, represented in FIG. 2, the disk-like membrane 13 of the float obturator 11 rests against the flat base 10 of the containment cage bush 8, so as to close the annular valve seat 15 and thus the outlet opening 4 of the drip chamber 1. This condition corresponds to the absence of liquid in the drip chamber 1.

Figure 3:
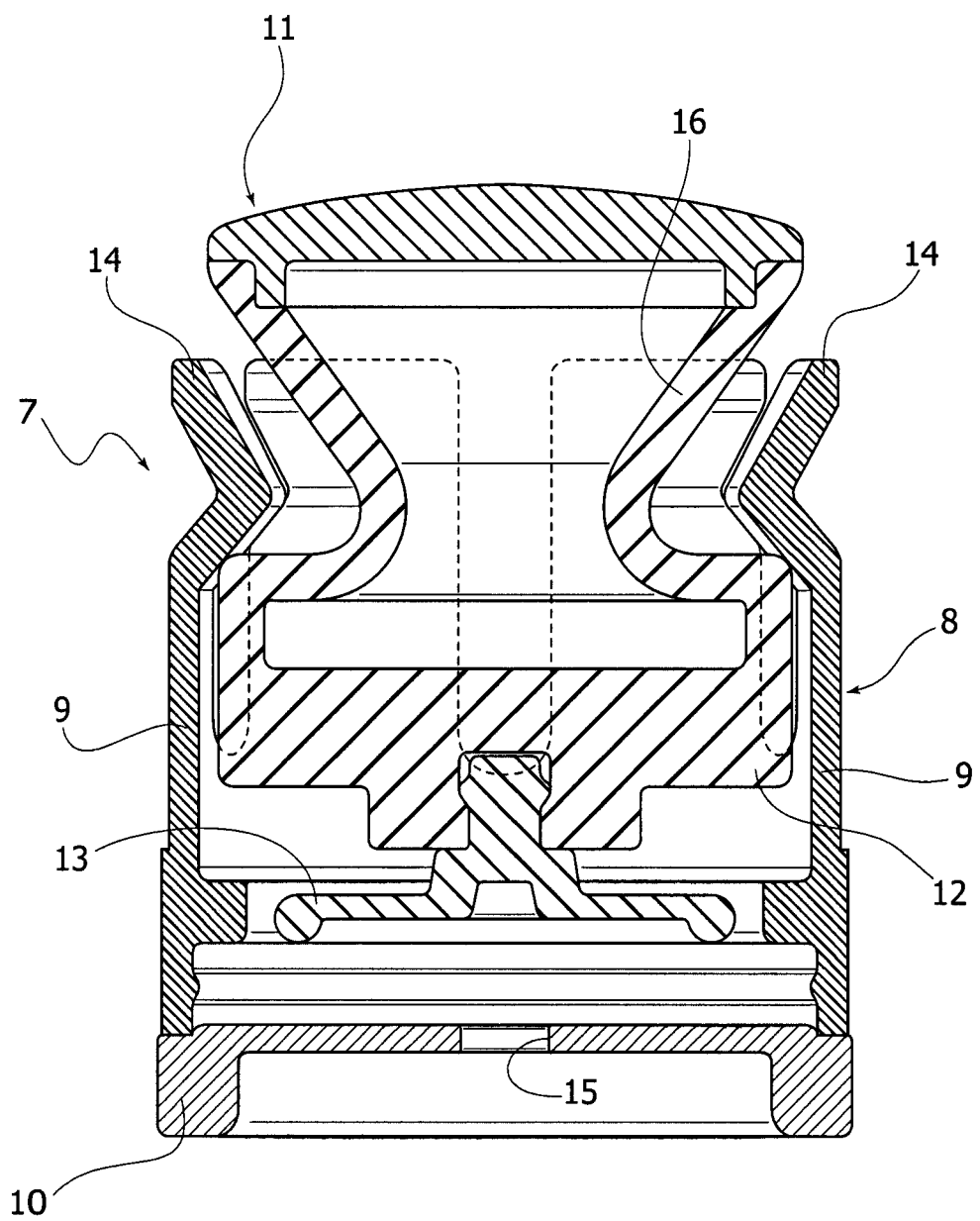
FIG. 3 shows—in larger detail—the foot valve in the opening position.
Figure 4:
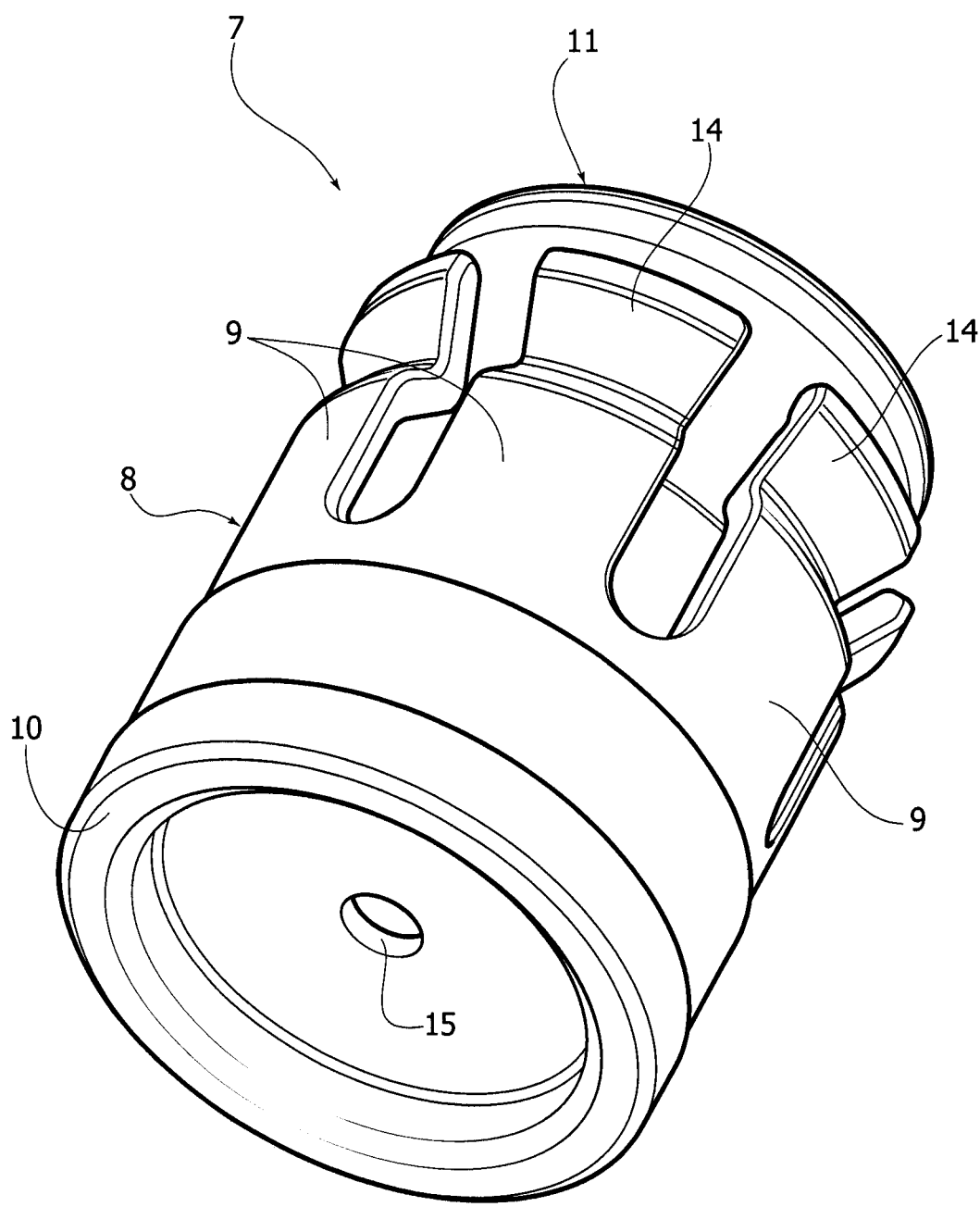
FIG. 4 is a perspective view of the foot valve.

In presence of liquid, the foot valve 7 takes the opening position represented in FIGS. 1 and 3: the float obturator 11 is displaced in the containment cage bush 8 in a position such that the disk-like membrane 13 is separated from the annular valve seat 15, so as to keep the passage open through the outlet opening 4 of the drip chamber 1.

The opening and closing displacements of the float obturator 11 are efficiently guided by the containment cage bush 8. In addition, the displacement thereof from the closing position to the opening position can be carried out in a comfortable and easy manner even manually, by simply applying a radial deformation to the elastically deformable lateral wall 2 of the drip chamber 1—using two fingers—so as to correspondingly radially deform the deformable axial sectors 9 of the containment cage bush 7 and transmit an axial thrust of the float obturator 11 in the direction of the end 6 of the drip chamber 1, due to the interaction between the free and diverging ends 14 and the diverging annular surface 16.

In the light of the description above, it is clear that the displacements of the float obturator 11 corresponding to the closing and opening of the foot valve 7 occur not only in an efficiently guided manner by the containment cage bush 8, but also for limited axial travels that contribute to ensuring a perfect closure and instantaneous re-opening of the foot valve 7.

Figure 5:
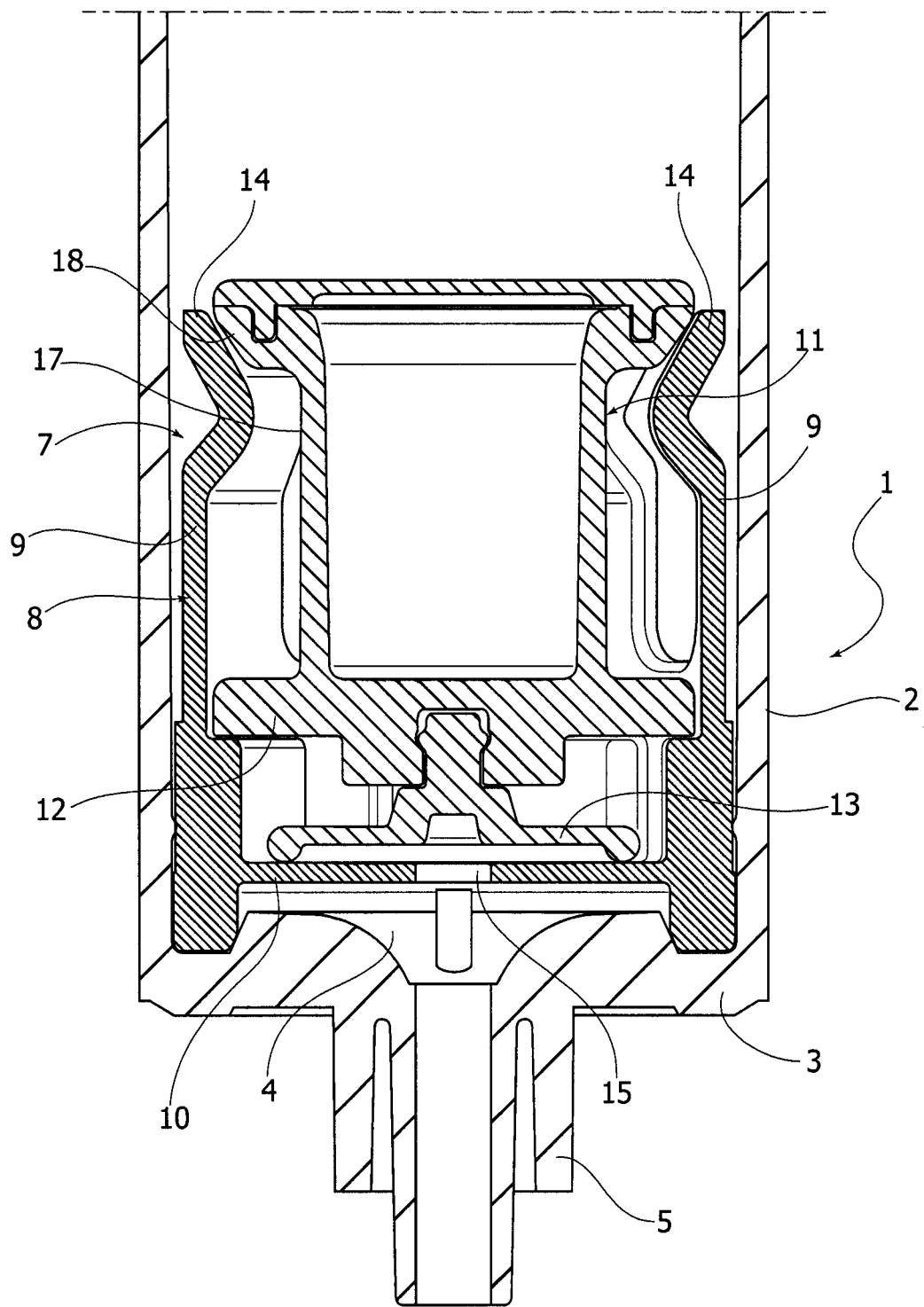
FIGS. 5 and 6 show, in axial section, a variant of the foot valve according to the invention respectively in closing position and in opening position.
Figure 6:
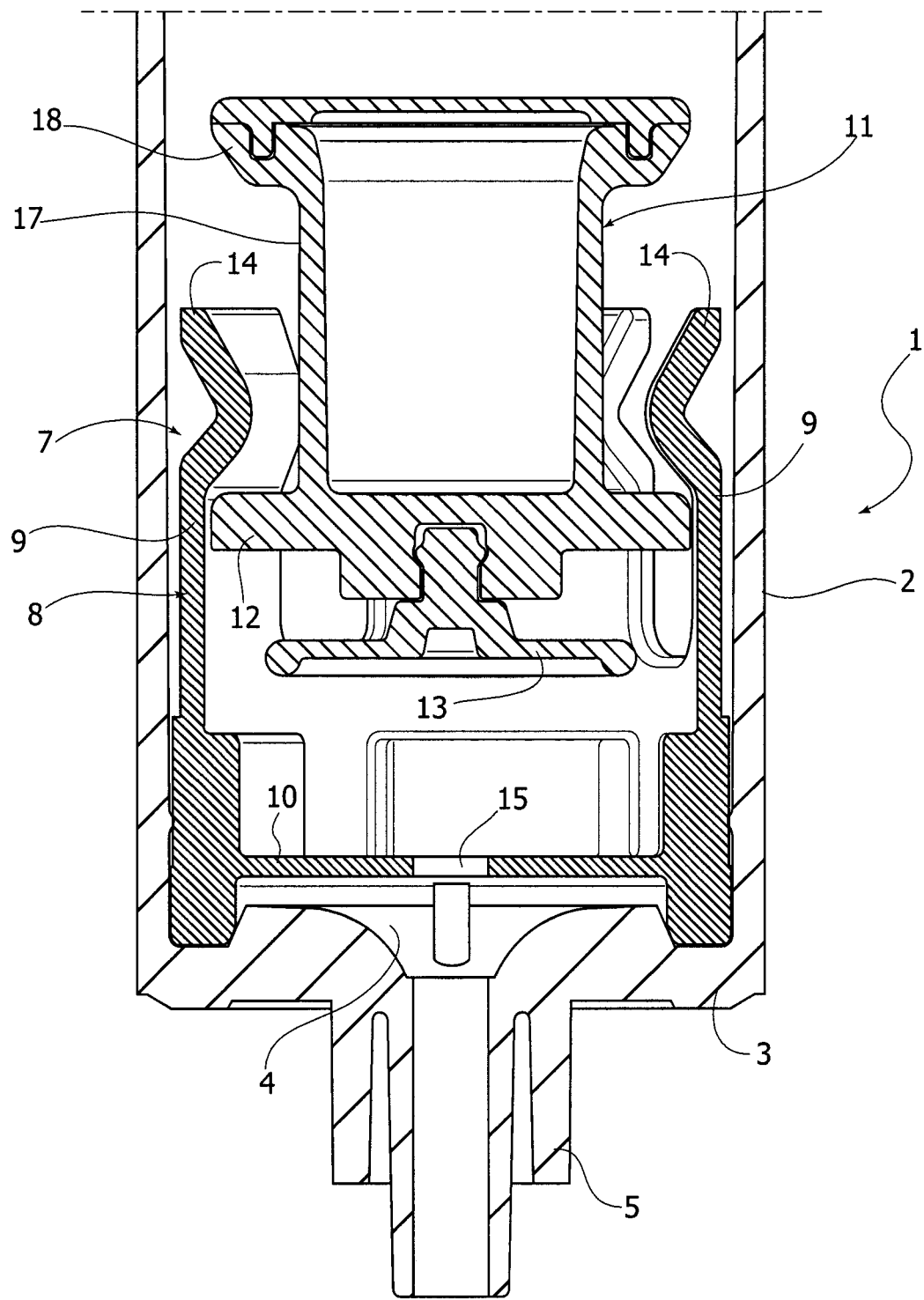

FIGS. 5 and 6 show a variant of the foot valve according to the invention, respectively represented in the opening position and in the closing position.

In such variant, currently considered the preferred embodiment, parts identical or similar to previously described ones are indicated using the same reference numbers. Its difference with respect to the previous embodiments lies in that the flat base 10 of the body of the float obturator 11 is made in a single piece with the lateral wall thereof, indicated with 17, having an elongated cylindrical shape. The upper end of the cylindrical wall 17, indicated with 18, is substantially radially turned towards the external and it has a rounded surface to cooperate with the diverging portions 14 of the deformable axial sectors 9 of the containment cage bush 8, in a manner similar to the previously described one.

Obviously, the construction details and the embodiments may widely vary with respect to what has been described and illustrated, without departing from the scope of protection of the present invention as defined in the claims that follow.

The invention claimed is:

1. Foot valve for drip chambers of medical infusion or transfusion apparatuses, comprising:
    an annular valve seat with which a float obturator which is axially displaceable between a closed position and an open position of the valve seat cooperates,
    a containment cage bush having an elastically deformable lateral wall within which said float obturator floats in a guided fashion,
    the lateral wall of the containment cage bush and the float obturator having respective mutually facing surfaces configured such that a radial deformation of the containment cage bush applies an axial thrust to the float obturator in the direction of moving the float obturator apart from said annular valve seat, and
    wherein the lateral wall of the containment cage bush is formed by a crown of elastically deformable axial sectors with free ends having diverging portions facing towards a corresponding diverging annular wall of the float obturator.

2. The valve according to claim 1, wherein the containment cage bush has a flat base forming said annular valve seat and said float obturator is provided with a soft disk-like membrane which rests against said flat base in said closing position.

3. Drip chamber for medical infusion or transfusion apparatuses, comprising:
    a hollow elongated cylindrical body having a radially elastically deformable lateral wall and a bottom wall provided with an outlet opening, and a foot valve including an annular valve seat facing said outlet opening and with which a float obturator which is axially displaceable between a position for closing and a position for opening the valve seat cooperates,
    the foot valve comprising a containment cage bush sealingly engaged between the lateral wall and the bottom wall of the drip chamber body and having an elastically deformable lateral wall within which said float obturator floats in a guided fashion,
    the lateral wall of the containment cage bush and the float obturator having respective mutually facing surfaces configured such that a radial deformation of the lateral wall of the drip chamber body and transmitted to the lateral wall of the containment cage bush applies an axial thrust to the float obturator in the direction of moving the float obturator apart from said annular valve seat,
    wherein the lateral wall of the containment cage bush is formed by a crown of elastically deformable axial sectors with free ends having diverging portions facing towards a corresponding diverging annular wall of the float obturator.

4. The drip chamber according to claim 3, wherein the containment cage bush has a flat base forming said annular valve seat and said float obturator is provided with a soft disk-like membrane which rests against said flat base in said closing position.

\* \* \* \* \*